US009856489B2

(12) United States Patent
Gomord et al.

(10) Patent No.: US 9,856,489 B2
(45) Date of Patent: Jan. 2, 2018

(54) METHOD FOR PRODUCING HIGH-QUALITY RECOMBINANT ALLERGENS IN A PLANT

(71) Applicant: ANGANY GENETICS, Rouen (FR)

(72) Inventors: Veronique Gomord, Rouen (FR); Anne Catherine Fitchette, Mesnil Panneville (FR); Loic Faye, St Jacques sur Darnetal (FR)

(73) Assignee: ANGANY GENETICS, Rouen (FR)

( * ) Notice: Subject to any disclaimer, the term of this patent is extended or adjusted under 35 U.S.C. 154(b) by 0 days.

(21) Appl. No.: 14/406,542

(22) PCT Filed: Jun. 13, 2013

(86) PCT No.: PCT/FR2013/051383
§ 371 (c)(1),
(2) Date: Dec. 9, 2014

(87) PCT Pub. No.: WO2013/186495
PCT Pub. Date: Dec. 19, 2013

(65) Prior Publication Data
US 2015/0361143 A1 Dec. 17, 2015

(30) Foreign Application Priority Data
Jun. 13, 2012 (FR) ...................................... 12 55510

(51) Int. Cl.
*C12N 15/82* (2006.01)
*C07H 21/04* (2006.01)

(52) U.S. Cl.
CPC ..... *C12N 15/8257* (2013.01); *C12N 15/8205* (2013.01)

(58) Field of Classification Search
None
See application file for complete search history.

(56) References Cited

U.S. PATENT DOCUMENTS

| | | | | |
|---|---|---|---|---|
| 4,036,756 A | * | 7/1977 | Dockery | A01K 63/045 137/142 |
| 7,947,871 B2 | * | 5/2011 | Shestibratov | C12N 15/8205 435/430 |
| 9,068,194 B2 | * | 6/2015 | Unkefer | C12N 9/80 |
| 2006/0077634 A1 | | 4/2006 | Chen et al. | |
| 2012/0192486 A1 | * | 8/2012 | Shanahan | A01G 9/26 47/58.1 LS |
| 2012/0284871 A1 | * | 11/2012 | Lomonossoff | C12N 15/8216 800/278 |
| 2014/0290135 A1 | * | 10/2014 | Carraro | C12N 15/8205 47/57.7 |
| 2016/0280747 A1 | * | 9/2016 | Skerra | C07K 14/435 |

FOREIGN PATENT DOCUMENTS

| | | | | |
|---|---|---|---|---|
| WO | WO 2007/123488 | * | 11/2007 | ............... C12N 1/21 |
| WO | 2008056265 A2 | | 5/2008 | |

OTHER PUBLICATIONS

Paul et al. Molecular pharming Future targets and aspirations. (2011) Human Vaccines; vol. 7; pp. 375-382.*
Shoji et al. Immunogenicity of hemagglutinin from A/Bar-headed Goose/Qinghai/1A/05 and A/Anjui/1/05 strains of H5N1 influenza viruses produced in *Nicotiana benthamiana* plants. (2009) Vaccine; vol. 27; pp. 3467-3470.*
Wikipedia "Venturi Effect".*
Fisher Scientific Catalog "Nalgene 6140-0010 Faucet Aspirator Vacuum Pump".*
Santi et al. Protection conferred by recombinant Yersinia pestis antigens produced by a rapid and highly scalable plant expression system. (2006) PNAS; vol. 103; pp. 861-866.*
International Search Report, dated Sep. 30, 2013, from corresponding PCT application.
Vezina et al., "Transient Co-Expression for Fast and High-Yield Production of Antibodies with Human-Like N-Glycans in Plants", Plant Biotechnology Journal, vol. 7, No. 5, pp. 442-455 (2009)—XP-002582248.
Obermeyer et al., "Over-Expression and Production Plant Allergens by Molecular Farming Strategies", Methods, vol. 32, No. 3, pp. 235-240 (2004)—XP004488973.
Santi et al., "Protection Conferred by Recombinant Yersinia Pestis Antigens Produced by a Rapid and Highly Scalable Plant Expression System", PNAS, vol. 103, No. 4, pp. 861-866 (2006)—XP008129743.
Obembe et al., "Advances in Plant Molecular Farming", Biotechnology Advances, vol. 29, No. 2, pp. 210-222 (2011)—XP028136133.
Gleba et al., "Magnifection—A New Platform for Expressing Recombinant Vaccines in Plants", vol. 23, No. 17-18, pp. 2042-2048 (2005)—XP055029853.
Musiychuk et al., "A Launch Vector for the Production of Vaccine Antigens in Plants", Influenza and Other Respiratory Viruses, vol. 1, No. 1, pp. 19-25 (2007)—XP009058889.
De Muynck et al., "Production of Anibodies in Plants: Status After Twenty Years", Plant Biotechnology Journal, vol. 8, No. 5, pp. 529-563 (2010)—XP055038516.

* cited by examiner

*Primary Examiner* — Cathy Kingdon Worley
(74) *Attorney, Agent, or Firm* — Young & Thompson

(57) ABSTRACT

A method for producing a recombinant protein in a plant, in particular a tobacco plant, preferably *Nicotiana benthamiana*, includes the following steps: a) culturing the plant aeroponically or hydroponically, preferably on mobile floats and under LED lighting; b) vacuum agroinfiltration of the plant obtained in a) by agrobacteria that include a DNA fragment coding for the recombinant protein; c) returning the plants to culturing after step b), under the same conditions as for step a); and d) extracting and purifying the recombinant protein from the aerial portions of the plants produced in step c).

17 Claims, 8 Drawing Sheets

Figure 8

Figure 1:
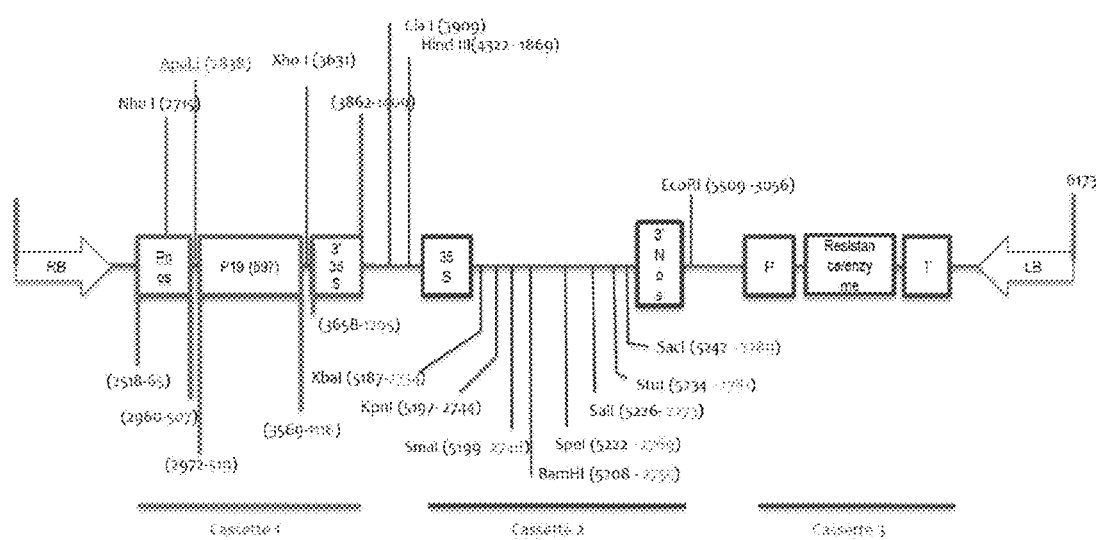

| Reozyme (SEQ ID NO:) | Sequence | LOCATION |
|---|---|---|
| 1 | MTGASRRSARGRI | ER |
| 2 | MARGERRRRA | ER |
| 3 | MNDRRPQRKRPA | ER |
| 4 | MTGASRRSAR GRIKSSSLSP GSDEGSAYPP SIRRGKGKEL VSIGAFKTNL KILVGLIILG IIVIYFVINR SLVRHGLLFDE SQKPRVITPF PAPKVMDLSM FQGEHKESLY WGTYRPHVYF GVRARTPLSL V6AGLMWLGYK DEMYVMRHFC | ER |
| 5 | MARGSRSVGS SSSKWRYCNP SYYLKRPKRL ALLFIVFVCV SFVFWDRQT | ER+GA |
| 6 | MARGSRSVGS SSSKWRYCNP SYYLKRPKRL ALLFIVFVCV SFVFWDRQTL VREHQVEISE LQKEVTDLKN LVODLNNKQG GISGKTDLGR KATKSSKDV | ER+GA |
| 7 | MAAALALLFIVFVCVSFVFWDR | ER+GA |
| 8 | MGVFSNLRGP RAGATHDEFP ATNGSPSSSS SPSSSIKRRL SNLLPLCVAL VVIAEIGFLG RLDKVATS | ER+GA |
| 9 | MRGYKFCCDF RYLLILAAVA FIYIQMRLFA TQSEYADR | ER+GA |
| 10 | MGVFSNLRCP KIGLTHEELP VVANGSTSSS SSPSSFKRKV STFLPICVAL VVIEIGFLC RLDNASTS | Medial Golgi |
| 11 | MLVMPQPPKP FNTITITIMI AFTFFLLFLT GFLQFPSISP S | Trans Golgi |
| 12 | MARGSRSVGS SSSKWRYCNP SYYLKRPKRL ALLFIVFVCV SFVFWCVSFV FWDRQTLVRE HQVEISELQK EVTDLKNLVD DLNNKQGGTS GKTDLGRKAT KSSKDV | Trans Golgi |
| 13 | XXXLALLFIVFVCVSFVFWDR | Cis Golgi |
| 14 | XXRYLLILAAVAFIYIQMRLFATQS | Cis Golgi |
| 15 | XXXLGILFAVTLSIVLMLVSVXXX | Cis-median Golgi |
| 16 | XXKIFLYMLLLNSLFLIIYFVFH | Median Golgi |
| 17 | XXXRKLSNLLPLCVALVVIAEIGFLG | Cis Golgi |
| 18 | XXXRKVSTFLPICVALVVIEIGFLC | Median Golgi |
| 19 | XXFNTITITIMIAFTFFLLFLTGFLQFXX | Trans Golgi |
| 20 | XXKRLALLFIVFVCVSFVFWCVSFVFWDR | Trans Golgi |

SEQUENCE LISTING

<160> NUMBER OF SEQ ID NOS: 22

<210> SEQ ID NO 1
<211> LENGTH: 13
<212> TYPE: PRT
<213> ORGANISM: Artificial Sequence
<220> FEATURE:

```
<223> OTHER INFORMATION: signal peptide

<400> SEQUENCE: 1

Met Thr Gly Ala Ser Arg Arg Ser Ala Arg Gly Arg Ile
1               5                   10

<210> SEQ ID NO 2
<211> LENGTH: 10
<212> TYPE: PRT
<213> ORGANISM: Artificial Sequence
<220> FEATURE:
<223> OTHER INFORMATION: signal peptide

<400> SEQUENCE: 2

Met Ala Arg Gly Glu Arg Arg Arg Arg Ala
1               5                   10

<210> SEQ ID NO 3
<211> LENGTH: 12
<212> TYPE: PRT
<213> ORGANISM: Artificial Sequence
<220> FEATURE:
<223> OTHER INFORMATION: signal peptide

<400> SEQUENCE: 3

Met Asn Asp Arg Arg Pro Gln Arg Lys Arg Pro Ala
1               5                   10

<210> SEQ ID NO 4
<211> LENGTH: 150
<212> TYPE: PRT
<213> ORGANISM: Artificial Sequence
<220> FEATURE:
<223> OTHER INFORMATION: signal peptide

<400> SEQUENCE: 4

Met Thr Gly Ala Ser Arg Arg Ser Ala Arg Gly Arg Ile Lys Ser Ser
1               5                   10                  15

Ser Leu Ser Pro Gly Ser Asp Glu Gly Ser Ala Tyr Pro Pro Ser Ile
                20                  25                  30

Arg Arg Gly Lys Gly Lys Glu Leu Val Ser Ile Gly Ala Phe Lys Thr
            35                  40                  45

Asn Leu Lys Ile Leu Val Gly Leu Ile Ile Leu Gly Ile Ile Val Ile
        50                  55                  60

Tyr Phe Val Ile Asn Arg Leu Val Arg His Gly Leu Leu Phe Asp Glu
65                  70                  75                  80

Ser Gln Lys Pro Arg Val Ile Thr Pro Phe Pro Ala Pro Lys Val Met
                85                  90                  95

Asp Leu Ser Met Phe Gln Gly Glu His Lys Glu Ser Leu Tyr Trp Gly
            100                 105                 110

Thr Tyr Arg Pro His Val Tyr Phe Gly Val Arg Ala Arg Thr Pro Leu
        115                 120                 125

Ser Leu Val Ala Gly Leu Met Trp Leu Gly Val Lys Asp Glu Met Tyr
    130                 135                 140

Val Met Arg His Phe Cys
145                 150

<210> SEQ ID NO 5
<211> LENGTH: 49
<212> TYPE: PRT
<213> ORGANISM: Artificial Sequence
<220> FEATURE:
```

<223> OTHER INFORMATION: signal peptide

<400> SEQUENCE: 5

Met Ala Arg Gly Ser Arg Ser Val Gly Ser Ser Ser Lys Trp Arg
1               5                   10                  15

Tyr Cys Asn Pro Ser Tyr Tyr Leu Lys Arg Pro Lys Arg Leu Ala Leu
            20                  25                  30

Leu Phe Ile Val Phe Val Cys Val Ser Phe Val Phe Trp Asp Arg Gln
        35                  40                  45

Thr

<210> SEQ ID NO 6
<211> LENGTH: 99
<212> TYPE: PRT
<213> ORGANISM: Artificial Sequence
<220> FEATURE:
<223> OTHER INFORMATION: signal peptide

<400> SEQUENCE: 6

Met Ala Arg Gly Ser Arg Ser Val Gly Ser Ser Ser Lys Trp Arg
1               5                   10                  15

Tyr Cys Asn Pro Ser Tyr Tyr Leu Lys Arg Pro Lys Arg Leu Ala Leu
            20                  25                  30

Leu Phe Ile Val Phe Val Cys Val Ser Phe Val Phe Trp Asp Arg Gln
        35                  40                  45

Thr Leu Val Arg Glu His Gln Val Glu Ile Ser Glu Leu Gln Lys Glu
    50                  55                  60

Val Thr Asp Leu Lys Asn Leu Val Asp Asp Leu Asn Asn Lys Gln Gly
65                  70                  75                  80

Gly Thr Ser Gly Lys Thr Asp Leu Gly Arg Lys Ala Thr Lys Ser Ser
                85                  90                  95

Lys Asp Val

<210> SEQ ID NO 7
<211> LENGTH: 22
<212> TYPE: PRT
<213> ORGANISM: Artificial Sequence
<220> FEATURE:
<223> OTHER INFORMATION: signal peptide

<400> SEQUENCE: 7

Met Ala Ala Ala Leu Ala Leu Leu Phe Ile Val Phe Val Cys Val Ser
1               5                   10                  15

Phe Val Phe Trp Asp Arg
            20

<210> SEQ ID NO 8
<211> LENGTH: 68
<212> TYPE: PRT
<213> ORGANISM: Artificial Sequence
<220> FEATURE:
<223> OTHER INFORMATION: signal peptide

<400> SEQUENCE: 8

Met Gly Val Phe Ser Asn Leu Arg Gly Pro Arg Ala Gly Ala Thr His
1               5                   10                  15

Asp Glu Phe Pro Ala Thr Asn Gly Ser Pro Ser Ser Ser Ser Ser Pro
            20                  25                  30

Ser Ser Ser Ile Lys Arg Lys Leu Ser Asn Leu Leu Pro Leu Cys Val
        35                  40                  45

```
Ala Leu Val Val Ile Ala Glu Ile Gly Phe Leu Gly Arg Leu Asp Lys
    50                  55                  60

Val Ala Thr Ser
65

<210> SEQ ID NO 9
<211> LENGTH: 38
<212> TYPE: PRT
<213> ORGANISM: Artificial Sequence
<220> FEATURE:
<223> OTHER INFORMATION: signal peptide

<400> SEQUENCE: 9

Met Arg Gly Tyr Lys Phe Cys Cys Asp Phe Arg Tyr Leu Leu Ile Leu
1               5                   10                  15

Ala Ala Val Ala Phe Ile Tyr Ile Gln Met Arg Leu Phe Ala Thr Gln
            20                  25                  30

Ser Glu Tyr Ala Asp Arg
        35

<210> SEQ ID NO 10
<211> LENGTH: 68
<212> TYPE: PRT
<213> ORGANISM: Artificial Sequence
<220> FEATURE:
<223> OTHER INFORMATION: signal peptide

<400> SEQUENCE: 10

Met Gly Val Phe Ser Asn Leu Arg Gly Pro Lys Ile Gly Leu Thr His
1               5                   10                  15

Glu Glu Leu Pro Val Val Ala Asn Gly Ser Thr Ser Ser Ser Ser Ser
            20                  25                  30

Pro Ser Ser Phe Lys Arg Lys Val Ser Thr Phe Leu Pro Ile Cys Val
        35                  40                  45

Ala Leu Val Val Ile Ile Glu Ile Gly Phe Leu Cys Arg Leu Asp Asn
    50                  55                  60

Ala Ser Thr Ser
65

<210> SEQ ID NO 11
<211> LENGTH: 41
<212> TYPE: PRT
<213> ORGANISM: Artificial Sequence
<220> FEATURE:
<223> OTHER INFORMATION: signal peptide

<400> SEQUENCE: 11

Met Leu Val Met Pro Gln Pro Pro Lys Pro Phe Asn Thr Ile Thr Ile
1               5                   10                  15

Thr Ile Met Ile Ala Phe Thr Phe Phe Leu Leu Phe Leu Thr Gly Phe
            20                  25                  30

Leu Gln Phe Pro Ser Ile Ser Pro Ser
        35                  40

<210> SEQ ID NO 12
<211> LENGTH: 106
<212> TYPE: PRT
<213> ORGANISM: Artificial Sequence
<220> FEATURE:
<223> OTHER INFORMATION: signal peptide

<400> SEQUENCE: 12
```

```
Met Ala Arg Gly Ser Arg Ser Val Gly Ser Ser Ser Lys Trp Arg
1               5                   10                  15

Tyr Cys Asn Pro Ser Tyr Tyr Leu Lys Arg Pro Lys Arg Leu Ala Leu
            20                  25                  30

Leu Phe Ile Val Phe Val Cys Val Ser Phe Val Phe Trp Cys Val Ser
            35                  40                  45

Phe Val Phe Trp Asp Arg Gln Thr Leu Val Arg Glu His Gln Val Glu
        50                  55                  60

Ile Ser Glu Leu Gln Lys Glu Val Thr Asp Leu Lys Asn Leu Val Asp
65              70                  75                  80

Asp Leu Asn Asn Lys Gln Gly Gly Thr Ser Gly Lys Thr Asp Leu Gly
                85                  90                  95

Arg Lys Ala Thr Lys Ser Ser Lys Asp Val
            100                 105

<210> SEQ ID NO 13
<211> LENGTH: 21
<212> TYPE: PRT
<213> ORGANISM: Artificial Sequence
<220> FEATURE:
<223> OTHER INFORMATION: signal peptide
<220> FEATURE:
<221> NAME/KEY: misc_feature
<222> LOCATION: (1)..(3)
<223> OTHER INFORMATION: Xaa can be any naturally occurring amino acid

<400> SEQUENCE: 13

Xaa Xaa Xaa Leu Ala Leu Leu Phe Ile Val Phe Val Cys Val Ser Phe
1               5                   10                  15

Val Phe Trp Asp Arg
                20

<210> SEQ ID NO 14
<211> LENGTH: 25
<212> TYPE: PRT
<213> ORGANISM: Artificial Sequence
<220> FEATURE:
<223> OTHER INFORMATION: signal peptide
<220> FEATURE:
<221> NAME/KEY: misc_feature
<222> LOCATION: (1)..(2)
<223> OTHER INFORMATION: Xaa can be any naturally occurring amino acid

<400> SEQUENCE: 14

Xaa Xaa Arg Tyr Leu Leu Ile Leu Ala Ala Val Ala Phe Ile Tyr Ile
1               5                   10                  15

Gln Met Arg Leu Phe Ala Thr Gln Ser
            20                  25

<210> SEQ ID NO 15
<211> LENGTH: 24
<212> TYPE: PRT
<213> ORGANISM: Artificial Sequence
<220> FEATURE:
<223> OTHER INFORMATION: signal peptide
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (22)..(24)
<223> OTHER INFORMATION: Xaa can be any naturally occurring amino acid

<400> SEQUENCE: 15
```

```
Xaa Xaa Xaa Leu Gly Ile Leu Phe Ala Val Thr Leu Ser Ile Val Leu
1               5                   10                  15

Met Leu Val Ser Val Xaa Xaa Xaa
            20
```

```
<210> SEQ ID NO 16
<211> LENGTH: 23
<212> TYPE: PRT
<213> ORGANISM: Artificial Sequence
<220> FEATURE:
<223> OTHER INFORMATION: signal peptide
<220> FEATURE:
<221> NAME/KEY: misc_feature
<222> LOCATION: (1)..(2)
<223> OTHER INFORMATION: Xaa can be any naturally occurring amino acid

<400> SEQUENCE: 16

Xaa Xaa Lys Ile Phe Leu Tyr Met Leu Leu Asn Ser Leu Phe Leu
1               5                   10                  15

Ile Ile Tyr Phe Val Phe His
            20
```

```
<210> SEQ ID NO 17
<211> LENGTH: 26
<212> TYPE: PRT
<213> ORGANISM: Artificial Sequence
<220> FEATURE:
<223> OTHER INFORMATION: signal petide
<220> FEATURE:
<221> NAME/KEY: misc_feature
<222> LOCATION: (1)..(3)
<223> OTHER INFORMATION: Xaa can be any naturally occurring amino acid

<400> SEQUENCE: 17

Xaa Xaa Xaa Arg Lys Leu Ser Asn Leu Leu Pro Leu Cys Val Ala Leu
1               5                   10                  15

Val Val Ile Ala Glu Ile Gly Phe Leu Gly
            20                  25
```

```
<210> SEQ ID NO 18
<211> LENGTH: 26
<212> TYPE: PRT
<213> ORGANISM: Artificial Sequence
<220> FEATURE:
<223> OTHER INFORMATION: signal peptide
<220> FEATURE:
<221> NAME/KEY: misc_feature
<222> LOCATION: (1)..(3)
<223> OTHER INFORMATION: Xaa can be any naturally occurring amino acid

<400> SEQUENCE: 18

Xaa Xaa Xaa Arg Lys Val Ser Thr Phe Leu Pro Ile Cys Val Ala Leu
1               5                   10                  15

Val Val Ile Ile Glu Ile Gly Phe Leu Cys
            20                  25
```

```
<210> SEQ ID NO 19
<211> LENGTH: 29
<212> TYPE: PRT
<213> ORGANISM: Artificial Sequence
<220> FEATURE:
<223> OTHER INFORMATION: signal peptide
<220> FEATURE:
<221> NAME/KEY: misc_feature
<222> LOCATION: (1)..(2)
<223> OTHER INFORMATION: Xaa can be any naturally occurring amino acid
<220> FEATURE:
```

```
<221> NAME/KEY: misc_feature
<222> LOCATION: (28)..(29)
<223> OTHER INFORMATION: Xaa can be any naturally occurring amino acid

<400> SEQUENCE: 19

Xaa Xaa Phe Asn Thr Ile Thr Ile Thr Ile Met Ile Ala Phe Thr Phe
1               5                   10                  15

Phe Leu Leu Phe Leu Thr Gly Phe Leu Gln Phe Xaa Xaa
            20                  25

<210> SEQ ID NO 20
<211> LENGTH: 29
<212> TYPE: PRT
<213> ORGANISM: Artificial Sequence
<220> FEATURE:
<223> OTHER INFORMATION: signal peptide
<220> FEATURE:
<221> NAME/KEY: misc_feature
<222> LOCATION: (1)..(2)
<223> OTHER INFORMATION: Xaa can be any naturally occurring amino acid

<400> SEQUENCE: 20

Xaa Xaa Lys Arg Leu Ala Leu Leu Phe Ile Val Phe Val Cys Val Ser
1               5                   10                  15

Phe Val Phe Trp Cys Val Ser Phe Val Phe Trp Asp Arg
            20                  25

<210> SEQ ID NO 21
<211> LENGTH: 12295
<212> TYPE: DNA
<213> ORGANISM: Artificial Sequence
<220> FEATURE:
<223> OTHER INFORMATION: plasmid pAG01

<400> SEQUENCE: 21
tgagcgtcgc aaaggcgctc ggtcttgcct tgctcgtcgg tgatgtactt caccagctcc      60
gcgaagtcgc tcttcttgat ggagcgcatg gggacgtgct tggcaatcac gcgcaccccc     120
cggccgtttt agcggctaaa aaagtcatgg ctctgccctc gggcggacca cgcccatcat     180
gaccttgcca agctcgtcct gcttctcttc gatcttcgcc agcagggcga ggatcgtggc     240
atcaccgaac cgcgccgtgc gcgggtcgtc ggtgagccag agtttcagca ggccgcccag     300
gcggcccagg tcgccattga tgcgggccag ctcgcggacg tgctcatagt ccacgacgcc     360
cgtgattttg tagccctggc cgacggccag caggtaggcc gacaggctca tgccggccgc     420
cgccgccttt tcctcaatcg ctcttcgttc gtctggaagg cagtacacct tgataggtgg     480
gctgcccttc ctggttggct tggtttcatc agccatccgc ttgccctcat ctgttacgcc     540
ggcggtagcc ggccagcctc gcagagcagg attcccgttg agcaccgcca ggtgcgaata     600
agggacagtg aagaaggaac accgctcgcg ggtgggcct  acttcaccta tcctgcccgg     660
ctgacgccgt tggatacacc aaggaaagtc tacacgaacc ctttggcaaa atcctgtata     720
tcgtgcgaaa aaggatggat ataccgaaaa aatcgctata atgaccccga agcagggtta     780
tgcagcggaa aagcgccacg cttcccgaag ggagaaaggc ggacaggtat ccggtaagcg     840
gcagggtcgg aacaggagag cgcacgaggg agcttccagg gggaaacgcc tggtatcttt     900
atagtcctgt cgggtttcgc cacctctgac ttgagcgtcg atttttgtga tgctcgtcag     960
gggggcggag cctatggaaa aacgccagca acgcggcctt tttacggttc ctggcctttt    1020
gctggccttt tgctcacatg ttctttcctg cgttatcccc tgattctgtg ataaccgta    1080 ttaccgcctt tgagtgagct gataccgctc gccgcagccg aacgaccgag cgcagcgagt    1140
```

```
cagtgagcga ggaagcggaa gagcgccaga aggccgccag agaggccgag cgcggccgtg    1200
aggcttggac gctagggcag ggcatgaaaa agcccgtagc gggctgctac gggcgtctga    1260
cgcggtggaa aggggagggg gatgttgtct acatggctct gctgtagtga gtgggttgcg    1320
ctccggcagc ggtcctgatc aatcgtcacc ctttctcggt ccttcaacgt tcctgacaac    1380
gagcctcctt ttcgccaatc catcgacaat caccgcgagt ccctgctcga acgctgcgtc    1440
cggaccggct tcgtcgaagg cgtctatcgc ggcccgcaac agcggcgaga gcggagcctg    1500
ttcaacggtg ccgccgcgct cgccggcatc gctgtcgccg gcctgctcct caagcacggc    1560
cccaacagtg aagtagctga ttgtcatcag cgcattgacg gcgtcccgg ccgaaaaacc     1620 cgcctcgcag aggaagcgaa gctgcgcgtc ggccgtttcc atctgcggtg cgcccggtcg    1680
cgtgccggca tggatgcgcg cgccatcgcg gtaggcgagc agcgcctgcc tgaagctgcg    1740
ggcattcccg atcagaaatg agcgccagtc gtcgtcggct ctcggcaccg aatgcgtatg    1800
attctccgcc agcatggctt cggccagtgc gtcgagcagc gcccgcttgt tcctgaagtg    1860
ccagtaaagc gccggctgct gaaccccccaa ccgttccgcc agtttgcgtg tcgtcagacc   1920
gtctacgccg acctcgttca acaggtccag ggcggcacgg atcactgtat tcggctgcaa    1980
ctttgtcatg cttgacactt tatcactgat aaacataata tgtccaccaa cttatcagtg    2040
ataaagaatc cgcgcgttca atcggaccag cggaggctgg tccggaggcc agacgtgaaa    2100
cccaacatac ccctgatcgt aattctgagc actgtcgcgc tcgacgctgt cggcatcggc    2160
ctgattatgc cggtgctgcc gggcctcctg cgcgatctgg ttcactcgaa cgacgtcacc    2220
gcccactatg gcattctgct ggcgctgtat gcgttggtgc aatttgcctg cgcacctgtg    2280
ctgggcgcgc tgtcggatcg tttcgggcgg cggccaatct tgctcgtctc gctggccggc    2340
gccagatctg gggaaccctg tggttggcat gcacatacaa atggacgaac ggataaacct    2400
tttcacgccc ttttaaatat ccgattattc taataaacgc tcttttctct taggtttacc    2460
cgccaatata tcctgtcaaa cactgatagt ttaaactgaa ggcgggaaac gacaatctga    2520
tcatgagcgg agaattaagg gagtcacgtt atgacccccg ccgatgacgc gggacaagcc    2580
gttttacgtt tggaactgac agaaccgcaa cgttgaagga gccactcagc cgcgggtttc    2640
tggagtttaa tgagctaagc acatacgtca gaaaccatta ttgcgcgttc aaaagtcgcc    2700
taaggtcact atcagctagc aaatatttct tgtcaaaaat gctccactga cgttccataa    2760
attcccctcg gtatccaatt agagtctcat attcactctc aatccaaata atctgcaccg    2820
gatctggatc gtttcgcgtg cacaaaaatg aacgagcta tacaaggaaa cgacgctagg     2880
gaacaagcta acagtgaacg ttgggatgga ggatcaggag gcaccacttc tcccttcaaa    2940
cttcctgacg aaagtccgag ttggactgag tggcggctac ataacgatga gacgaactcg    3000
aatcaagata tccccttgg tttcaaggaa agctggggtt tcgggaaagt tgtatttaag     3060
agatatctca gatacgacag gacgaagcc tcactgcaca gagtccttgg atcttggacg     3120
ggagattcgg ttaactatgc agcatctcga ttttcggtt tcgaccagat cggatgtacc     3180
tatagtattc ggtttcgagg agttagtatc accgtttctg gagggtcgcg aactcttcag    3240
catctctgtg agatggcaat tcggtctaag caagaactgc tacagcttgc cccaatcgaa    3300
gtggaaagta atgtatcaag aggatgccct gaaggtactg agaccttcga aaaagaaagc    3360
gagtaagcgg gactctgggg ttcgaaatga ccgaccatat cttgctgcgt tcggatattt    3420
tcgtggagtt cccgccacag acccggatga tcccctaatt cggggatct ggattttagt     3480
```

| | |
|---|---|
| actggatttt ggttttagga attagaaatt ttattgatag aagtatttta caaatacaaa | 3540 |
| tacatactaa gggtttctta tatgctcaac acatgagcga aaccctatag gaaccctaat | 3600 |
| tcccttatct gggaactact cacacattat tatggagaaa ctcgagcttg tcgatcgacc | 3660 |
| ctcctgtcaa tgctggcggc ggctctggtg gtggttctgg tggcggctct gagggtggtg | 3720 |
| gctctgaggg tggcggttct gagggtggcg gctctgaggg aggcggttcc ggtggtggct | 3780 |
| ctggttccgg tgattttgat tatgaaaaga tggcaaacgc taataagggg gctatgaccg | 3840 |
| aaaatgccga tgaaaacgcg ctacagtctg acgctaaagg caaacttgat tctgtcgcta | 3900 |
| ctgattacgg tgctgctatc gatggtttca ttggtgacgt ttccggcctt gctaatggta | 3960 |
| atggtgctac tggtgatttt gctggctcta attcccaaat ggctcaagtc ggtgacggtg | 4020 |
| ataattcacc tttaatgaat aatttccgtc aatatttacc ttccctccct caatcggttg | 4080 |
| aatgtcgccc ttttgtcttt ggcccaatac gcaaaccgcc tctccccgcg cgttggccga | 4140 |
| ttcattaatg cagctggcac gacaggtttc ccgactggaa agcgggcagt gagcgcaacg | 4200 |
| caattaatgt gagttagctc actcattagg cacccccagg ctttacactt tatgcttccgg | 4260 |
| ctcgtatgtt gtgtggaatt gtgagcggat aacaatttca cacaggaaac agctatgacc | 4320 |
| atgattacgc caagcttgca tgcctgcagg tccccagatt agccttttca atttcagaaa | 4380 |
| gaatgctaac ccacagatgg ttagagaggc ttacgcagca ggtctcatca agacgatcta | 4440 |
| cccgagcaat aatctccagg aaatcaaata ccttcccaag aaggttaaag atgcagtcaa | 4500 |
| aagattcagg actaactgca tcaagaacac agagaaagat atatttctca agatcagaag | 4560 |
| tactattcca gtatggacga ttcaaggctt gcttcacaaa ccaaggcaag taatagagat | 4620 |
| tggagtctct aaaaaggtag ttcccactga atcaaaggcc atggagtcaa agattcaaat | 4680 |
| agaggaccta acagaactcg ccgtaaagac tggcgaacag ttcatacaga gtctcttacg | 4740 |
| actcaatgac aagaagaaaa tcttcgtcaa catggtggag cacgacacac ttgtctactc | 4800 |
| caaaaatatc aaagatacag tctcagaaga ccaaagggca attgagactt ttcaacaaag | 4860 |
| ggtaatatcc ggaaacctcc tcggattcca ttgcccagct atctgtcact ttattgtgaa | 4920 |
| gatagtggaa aaggaaggtg gctcctacaa atgccatcat tgcgataaag gaaaggccat | 4980 |
| cgttgaagat gcctctgccg acagtggtcc caaagatgga cccccaccca cgaggagcat | 5040 |
| cgtggaaaaa gaagacgttc caaccacgtc ttcaaagcaa gtggattgat gtgatatctc | 5100 |
| cactgacgta agggatgacg cacaatccca ctatccttcg caagacccct tcctctatata | 5160 |
| aggaagttca tttcatttgg agagaacacg ggggactcta gaggtacccg gcccgcggga | 5220 |
| tccgcggccg cactagtcga caggcctgag ctcgaatttc cccgatcgtt caaacatttg | 5280 |
| gcaataaagt ttcttaagat tgaatcctgt tgccggtctt gcgatgatta tcatataatt | 5340 |
| tctgttgaat tacgttaagc atgtaataat taacatgtaa tgcatgacgt tatttatgag | 5400 |
| atgggttttt atgattagag tcccgcaatt atacatttaa tacgcgatag aaaacaaaat | 5460 |
| atagcgcgca aactaggata aattatcgcg cgcggtgtca tctatgttac tagatcggga | 5520 |
| attcactggc cgtcgtttta caacgtcgtg actgggaaaa ccctggcgtt acccaactta | 5580 |
| atcgccttgc agcacatccc cctttcgcca gctggcgtaa tagcgaagag gcccgcaccg | 5640 |
| atcgcccttc ccaacagttg cgcagcctga atggcgcccg ctcctttcgc tttcttccct | 5700 |
| tcctttctcg ccacgttcgc cggctttccc cgtcaagctc taaatcgggg gctcccttta | 5760 |
| gggttccgat ttagtgcttt acggcacctc gaccccaaaa aacttgattt gggtgatggt | 5820 |
| tcacgtagtg ggccatcgcc ctgatagacg gttttcgcc ctttgacgtt ggagtccacg | 5880 |

```
ttctttaata gtggactctt gttccaaact ggaacaacac tcaaccctat ctcgggctat    5940
tcttttgatt tataagggat tttgccgatt tcggaaccac catcaaacag gattttcgcc    6000
tgctggggca aaccagcgtg gaccgcttgc tgcaactctc tcagggccag gcggtgaagg    6060
gcaatcagct gttgcccgtc tcactggtga aagaaaaac cacccagta cattaaaaac     6120 gtccgcaatg tgttattaag ttgtctaagc gtcaatttgt ttacaccaca atatatcctg    6180
ccaccagcca gccaacagct ccccgaccgg cagctcggca caaatcacc actcgataca     6240 ggcagcccat cagtccggga cggcgtcagc gggagagccg ttgtaaggcg gcagactttg    6300
ctcatgttac cgatgctatt cggaagaacg gcaactaagc tgccgggttt gaaacacgga    6360
tgatctcgcg gagggtagca tgttgattgt aacgatgaca gagcgttgct gcctgtgatc    6420
aaatatcatc tccctcgcag agatccgaat tatcagcctt cttattcatt tctcgcttaa    6480
ccgtgacagg ctgtcgatct tgagaactat gccgacataa taggaaatcg ctggataaag    6540
ccgctgagga agctgagtgg cgctatttct ttagaagtga acgttgacga tatcaactcc    6600
cctatccatt gctcaccgaa tggtacaggt cggggacccg aagttccgac tgtcggcctg    6660
atgcatcccc ggctgatcga ccccagatct ggggctgaga aagcccagta aggaaacaac    6720
tgtaggttcg agtcgcgaga tcccccggaa ccaaaggaag taggttaaac ccgctccgat    6780
caggccgagc cacgccaggc cgagaacatt ggttcctgta ggcatcggga ttggcggatc    6840
aaacactaaa gctactggaa cgagcagaag tcctccggcc gccagttgcc aggcggtaaa    6900
ggtgagcaga ggcacgggag gttgccactt gcgggtcagc acggttccga acgccatgga    6960
aaccgccccc gccaggcccg ctgcgacgcc gacaggatct agcgctgcgt ttggtgtcaa    7020
caccaacagc gccacgcccg cagttccgca aatagccccc aggaccgcca tcaatcgtat    7080
cgggctacct agcagagcgg cagagatgaa cacgaccatc agcggctgca cagcgcctac    7140
cgtcgccgcg accccgcccg gcaggcggta gaccgaaata acaacaagc tccagaatag     7200 cgaaatatta agtgcgccga ggatgaagat gcgcatccac cagattcccg ttggaatctg    7260
tcggacgatc atcacgagca ataaacccgc cggcaacgcc cgcagcagca taccggcgac    7320
ccctcggcct cgctgttcgg gctccacgaa acgccggac agatgcgcct tgtgagcgtc     7380 cttgggccg tcctcctgtt tgaagaccga cagcccaatg atctcgccgt cgatgtaggc      7440
gccgaatgcc acggcatctc gcaaccgttc agcgaacgcc tccatgggct ttttctcctc    7500
gtgctcgtaa acggacccga acatctctgg agctttcttc agggccgaca atcggatctc    7560
gcggaaatcc tgcacgtcgg ccgctccaag ccgtcgaatc tgagccttaa tcacaattgt    7620
caattttaat cctctgttta tcggcagttc gtagagcgcg ccgtgcgtcc gagcgatac     7680 tgagcgaagc aagtgcgtcg agcagtgccc gcttgttcct gaaatgccag taaagcgctg    7740
gctgctgaac ccccagccgg aactgacccc acaaggccct agcgtttgca atgcaccagg    7800
tcatcattga cccaggcgtg ttccaccagg ccgctgcctc gcaactcttc gcaggcttcg    7860
ccgacctgct cgcgccactt cttcacgcgg gtggaatccg atccgcacat gaggcggaag    7920
gtttccagct tgagcgggta cggctcccgg tgcgagctga aatagtcgaa catccgtcgg    7980
gccgtcggcg acagcttgcg gtacttctcc catatgaatt tcgtgtagtg gtcgccagca    8040
aacagcacga cgatttcctc gtcgatcagg acctggcaac gggacgtttt cttgccacgg    8100
tccaggacgc ggaagcggtg cagcagcgac accgattcca ggtgcccaac gcggtcggac    8160
gtgaagccca tcgccgtcgc ctgtaggcgc gacaggcatt cctcggcctt cgtgtaatac    8220
```

```
cggccattga tcgaccagcc caggtcctgg caaagctcgt agaacgtgaa ggtgatcggc    8280
tcgccgatag gggtgcgctt cgcgtactcc aacacctgct gccacaccag ttcgtcatcg    8340
tcggcccgca gctcgacgcc ggtgtaggtg atcttcacgt ccttgttgac gtggaaaatg    8400
accttgtttt gcagcgcctc gcgcgggatt ttcttgttgc gcgtggtgaa cagggcagag    8460
cgggccgtgt cgtttggcat cgctcgcatc gtgtccggcc acggcgcaat atcgaacaag    8520
gaaagctgca tttccttgat ctgctgcttc gtgtgtttca gcaacgcggc ctgcttggcc    8580
tcgctgacct gttttgccag gtcctcgccg gcggttttc gcttcttggt cgtcatagtt     8640
cctcgcgtgt cgatggtcat cgacttcgcc aaacctgccg cctcctgttc gagacgacgc    8700
gaacgctcca cggcggccga tggcgcgggc agggcagggg gagccagttg cacgctgtcg    8760
cgctcgatct tggccgtagc ttgctggacc atcgagccga cggactggaa ggtttcgcgg    8820
ggcgcacgca tgacggtgcg gcttgcgatg gtttcggcat cctcggcgga aaaccccgcg    8880
tcgatcagtt cttgcctgta tgccttccgg tcaaacgtcc gattcattca ccctccttgc    8940
gggattgccc cgactcacgc cggggcaatg tgcccttatt cctgatttga cccgcctggt    9000
gccttggtgt ccagataatc caccttatcg gcaatgaagt cggtcccgta gaccgtctgg    9060
ccgtccttct cgtacttggt attccgaatc ttgccctgca cgaataccag cgacccctgc    9120
cccaaatact tgccgtgggc ctcggcctga gagccaaaac acttgatgcg gaagaagtcg    9180
gtgcgctcct gcttgtcgcc ggcatcgttg cgccacatct aggtactaaa acaattcatc    9240
cagtaaaata taatatttta ttttctccca atcaggcttg atccccagta agtcaaaaaa    9300
tagctcgaca tactgttctt ccccgatatc ctccctgatc gaccggacgc agaaggcaat    9360
gtcataccac ttgtccgccc tgccgcttct cccaagatca ataaagccac ttactttgcc    9420
atctttcaca aagatgttgc tgtctcccag gtcgccgtgg aaaagacaa gttcctcttc      9480 gggcttttcc gtctttaaaa aatcatacag ctcgcgcgga tctttaaatg gagtgtcttc    9540
ttcccagttt tcgcaatcca catcggccag atcgttattc agtaagtaat ccaattcggc    9600
taagcggctg tctaagctat tcgtataggg acaatccgat atgtcgatgg agtgaaagag    9660
cctgatgcac tccgcataca gctcgataat cttttcaggg cttttgttcat cttcatactc   9720 ttccgagcaa aggacgccat cggcctcact catgagcaga ttgctccagc catcatgccg    9780
ttcaaagtgc aggacctttg gaacaggcag cttttccttcc agccatagca tcatgtcctt    9840
ttcccgttcc acatcatagg tggtcccttt ataccggctg tccgtcattt ttaaatatag    9900
gttttcattt tctcccacca gcttatatac cttagcagga gacattcctt ccgtatcttt    9960
tacgcagcgg tatttttcga tcagtttttt caattccggt gatattctca ttttagccat   10020
ttattatttc cttcctctt tctacagtat ttaaagatac cccaagaagc taattataac    10080
aagacgaact ccaattcact gttccttgca ttctaaaacc ttaaatacca gaaaacagct   10140
ttttcaaagt tgttttcaaa gttggcgtat aacatagtat cgacggagcc gattttgaaa   10200
ccacaattat gggtgatgct gccaacttac tgatttagtg tatgatggtg ttttttgaggt  10260 gctccagtgg cttctgtgtc tatcagctgt ccctcctgtt cagctactga cggggtggtg   10320
cgtaacggca aaagcaccgc cggacatcag cgctatctct gctctcactg ccgtaaaaca   10380
tggcaactgc agttcactta caccgcttct caacccggta cgcaccagaa aatcattgat   10440
atggccatga atggcgttgg atgccgggca acagcccgca ttatgggcgt tggcctcaac   10500 acgatttac gtcacttaaa aaactcaggc cgcagtcggt aacctcgcgc atacagccgg    10560
gcagtgacgt catcgtctgc gcggaaatgg acgaacagtg gggctatgtc ggggctaaat   10620
```

-continued

```
cgcgccagcg ctggctgttt tacgcgtatg acagtctccg aagacggtt gttgcgcacg      10680 tattcggtga acgcactatg gcgacgctgg ggcgtcttat gagcctgctg tcacccttg      10740 acgtggtgat atggatgacg gatggctggc cgctgtatga atcccgcctg aagggaaagc    10800
tgcacgtaat cagcaagcga tatacgcagc gaattgagcg gcataacctg aatctgaggc    10860
agcacctggc acggctggga cggaagtcgc tgtcgttctc aaaatcggtg gagctgcatg    10920
acaaagtcat cggcattat ctgaacataa aacactatca ataagttgga gtcattaccc     10980
aattatgata gaatttacaa gctataaggt tattgtcctg ggtttcaagc attagtccat    11040
gcaagttttt atgctttgcc cattctatag atatattgat aagcgcgctg cctatgcctt    11100 gcccctgaa atccttacat acggcgatat cttctatata aagatatat tatcttatca     11160 gtattgtcaa tatattcaag gcaatctgcc tcctcatcct cttcatcctc ttcgtcttgg    11220 tagctttta aatatggcgc ttcatagagt aattctgtaa aggtccaatt ctcgttttca     11280
tacctcggta taatcttacc tatcactca aatggttcgc tgggttatc gcaccccga       11340 acacgagcac ggcacccgcg accactatgc caagaatgcc caagtaaaa attgccggcc     11400 ccgccatgaa gtccgtgaat gccccgacgg ccgaagtgaa gggcaggccg ccacccaggc    11460
cgccgccctc actgcccggc acctggtcgc tgaatgtcga tgccagcacc tgcggcacgt    11520
caatgcttcc gggcgtcgcg ctcgggctga tcgcccatcc cgttactgcc ccgatcccgg    11580
caatggcaag gactgccagc gctgccattt ttggggtgag gccgttcgcg gccgaggggc    11640
gcagcccctg ggggatggg aggcccgcgt tagcggccg ggagggttcg agaagggggg      11700 gcaccccct tcggcgtgcg cggtcacgcg cacagggcgc agccctggtt aaaaacaagg     11760
tttataaata ttggtttaaa agcaggttaa aagacaggtt agcggtggcc gaaaaacggg    11820
cggaaaccct tgcaaatgct ggattttctg cctgtggaca gcccctcaaa tgtcaatagg    11880
tgcgcccctc atctgtcagc actctgcccc tcaagtgtca aggatcgcgc ccctcatctg    11940
tcagtagtcg cgcccctcaa gtgtcaatac cgcaggcac ttatccccag gcttgtccac     12000
atcatctgtg ggaaactcgc gtaaaatcag gcgttttcgc cgatttgcga ggctggccag    12060
ctccacgtcg ccggccgaaa tcgagcctgc ccctcatctg tcaacgccgc gccgggtgag    12120
tcggcccctc aagtgtcaac gtccgcccct catctgtcag tgagggccaa gttttccgcg    12180
aggtatccac aacgccggcg gccgcggtgt ctcgcacacg gcttcgacgg cgtttctggc    12240
gcgtttgcag ggccatagac ggccgccagc ccagcggcga gggcaaccag cccgg         12295
```

<210> SEQ ID NO 22
<211> LENGTH: 34
<212> TYPE: PRT
<213> ORGANISM: Artificial Sequence
<220> FEATURE:
<223> OTHER INFORMATION: Histidine tag

<400> SEQUENCE: 22

```
His His His His His His Thr Arg Pro Leu Glu Gln Lys Leu Ile Ser
1               5                   10                  15

Glu Glu Asp Leu Ala Ala Asn Asp Ile Leu Asp Tyr Lys Asp Asp Asp
            20                  25                  30

Asp Lys
```

METHOD FOR PRODUCING HIGH-QUALITY RECOMBINANT ALLERGENS IN A PLANT

The present invention relates to a method for producing high-quality recombinant allergens.

The use of recombinant allergens allows greater specificity and better efficacy of diagnostic tests and treatment of allergies.

Numerous allergens have already been produced in recombinant form. Today they are used for in vitro diagnosis of allergies. However, the expression system used, generally *E. coli*, most often only allows very approximate copies of the natural allergens to be obtained, owing to the inability of this bacterium to perform the post-translational modifications necessary for correct folding of proteins of eukaryotes. This often has an adverse effect on the reliability and sensitivity of the diagnostic tests carried out using these molecules, since certain epitopes able to react with patients' immunoglobulins E (IgE) are not present on the recombinant allergens produced in *E. coli*.

Eukaryotic expression systems have also been used for producing recombinant allergens. These are most often yeasts, and in this case hyperglycosylation, specific to these organisms, still does not allow production of recombinant allergens conforming with their natural homologs.

Plants are the only eukaryotic hosts allowing production of complex allergens in recombinant form, with production costs and quality compatible with their use for personalized treatment of allergies, integrating diagnostic tests and therapy.

However, the plant expression systems used so far for producing recombinant allergens generally employ plant transgenesis with its fundamental limits that are well known, namely:
  long times for transition from the gene to the protein, meaning that the development work takes several years, and
  low yields, of the order of 0.1% to 1% of the soluble proteins, meaning processing of a large volume of biomass of plant material for large-scale production.

Recent advances achieved using transient expression have made it possible to exceed these limits, on the one hand by greatly reducing the delays in passage from the gene to the protein, which allows much faster development, and on the other hand by increasing the production yields by at least a factor of 10, which minimizes the costs for extraction and purification of the protein of interest.

A technique of this kind for transient expression in plants is now used on a large scale for producing vaccines by certain companies, which are currently developing extensive production units in the United States.

However, despite these efforts, there is still a need for an efficient and reproducible method for producing recombinant allergens that allows recombinant allergens to be obtained having a composition and conformation similar to those of their natural homologs. Moreover, there is a need for a method that has a good production yield.

The present invention makes it possible to obtain complex recombinant proteins, in particular complex recombinant allergens, which have never been obtained previously in recombinant form. These allergens are, moreover, copies identical to their natural homologs.

The present invention therefore relates to a method for producing a recombinant protein in a plant, preferably a tobacco plant, preferably *Nicotiana benthamiana*, comprising the following steps:

a) culturing the plants aeroponically or hydroponically, preferably on mobile floats, and under LED lighting,
  b) agroinfiltration of the plants obtained in step a), under vacuum, by agrobacteria comprising a DNA fragment coding for the recombinant protein, then
  c) returning the plants to culturing after step b), in the same conditions as for step a), then
  d) extraction and purification of the recombinant protein from the aerial parts of the plants produced in step c).

The present invention also relates to a recombinant protein obtainable by the method according to the invention.

The plant usable in the method according to the invention is notably a tobacco plant selected from *Nicotiana benthamiana* and *Nicotiana tabacum* or any other plant usable for transient expression, such as a lettuce (genus *Lactuca*) or a spinach plant (*Spinacia oleracea*). Among the lettuces, we may mention the lettuce Appia, Grosse Blonde Paresseuse, Lollo Rosso, Merveille de quatre saisons ["four-seasons Wonder"], feuille de chêne [oak leaf lettuce], or red sails. The plant may also be of the genus *Arabidopsis*, or a mutant thereof, in particular glycosylation mutants of *Arabidopsis*; finally, it is possible to use knock-out tobacco plants (especially of glycosylation mutants).

Preferably, the recombinant protein produced by the method according to the invention is a recombinant allergen, preferably a recombinant mite allergen.

"Allergen" means any protein or any peptide capable of triggering an allergic reaction in a subject previously sensitized when he is in contact with it, most often by contact with the skin, inhalation or ingestion. An allergen is said to be "major" when a purified antigen triggers an allergy in 50% or more of the patients tested, and when it displays specific IgEs, with immediately positive skin tests, at a very low concentration, in at least 70% of subjects having an allergy to this allergen.

"Protein" means a sequence comprising at least 50 amino acids.

"Peptide" means a sequence comprising between 1 and 49 amino acids, preferably between 2 and 40 amino acids.

Preferably, the recombinant protein produced by the method according to the invention is an allergen, an allergen fragment or a fusion protein comprising an allergen or an allergen fragment.

Preferably, the recombinant protein is selected from the allergens responsible for respiratory allergies due to house dust mites, such as *Dermatophagoides farinae*, *Dermatophagoides pteronyssinus* or *Euroglyphus manei*, the allergens of storage mites such as *Blomia tropicalis*, the allergens of mites of the type *Acarus siro* (formerly called *Tyroglyphus farinae*), cockroach allergens, tree or grass pollen allergens, allergens from animals (cat, dog, horse), allergens of molds, the allergens responsible for contact allergies such as those of hevea latex or the allergens responsible for food allergies (milk, egg, fish, fruit).

Among the allergens of *Dermatophagoides farinae*, we may mention Der f 10, Der f 11, Der f 13, Der f 14, Der f 15, Der f 16, Der f 17, Der f 18, Der f 2, Der f 2.0101, Der f 2.0102, Der f 2.0103, Der f 2.0104, Der f 2.0105, Der f 2.0106, Der f 2.0107, Der f 2.0108, Der f 2.0109, Der f 2.0110, Der f 2.0111, Der f 2.0112, Der f 2.0113, Der f 2.0114, Der f 2.0115, Der f 2.0116, Der f 2.0117, Der f 20, Der f 3, Der f 4, Der f 5, Der f 6, Der f 7, Der f 8, Der f 9 and Der f HSP70.

Among the allergens of *Dermatophagoides pteronyssinus*, we may mention Der p 10, Der p 11, Der p 14, Der p 15, Der p 18, Der p 2, Der p 2.0101, Der p 2.0102, Der p 2.0103, Der p 2.0104, Der p 2.0105, Der p 2.0106, Der p 2.0107, Der p 2.0108, Der p 2.0109, Der p 2.0110, Der p 2.0111, Der p 2.0112, Der p 2.0113, Der p 20, Der p 21, Der p 3, Der p 4, Der p 5, Der p 6, Der p 7, Der p 8, Der p 9.

Among the allergens of *Blomia tropicalis*, we may mention Blo t 1, Blo t 5 (which has 40% sequence homology with Der p 5), Blo t 9, Blo t 10, Blo t 12 or Blo t 21.

All these allergens are well known, and their sequence may be found notably in databases such as Allergome (allergome.org), or quite simply in UniProt.

The method for producing recombinant allergens by transient expression according to the invention, notably in *N. benthamiana*, is very effective, reproducible, and has a good yield.

The method for producing recombinant proteins according to the invention comprises a first step of culturing the plant (step a), aeroponically or hydroponically, preferably in culture on free mobile floats, and under LED lighting, in order to cause it to produce the recombinant protein. Aeroponics corresponds to culture of the plant on a support, generally made of plastic, combined with constant misting with nutrient solutions based on mineral salts.

Hydroponics corresponds to culture of the plant without soil. The plant is cultured on a neutral, inert substrate, such as sand, clay beads, polystyrene plates or rock wool. The substrate is regularly irrigated with a stream of solution that supplies mineral salts and essential nutrients to the plant. In the method used according to the invention, tobacco plants, notably *N. benthamiana*, are cultured preferably hydroponically on free floats, for example on a plate of perforated polystyrene. These floats are arranged in tanks containing a culture medium that is constantly aerated by air diffusers. This technique allows standardization of the conditions for production of the recombinant proteins, combined with complete absence of risk of contamination of the agroinfiltration media in step b) by impurities or debris from the substrates contained in the pots (in the case of conventional culture). Moreover, the use of this culture system makes it possible to reach far higher yields, as is shown in the examples.

Finally, during scale-up, manipulation for agroinfiltration or harvesting of batches of plants fixed on a polystyrene plate is of course easier than that of pot and substrate cultured plants.

The method for producing recombinant proteins according to the invention comprises, after step a), a step b) of agroinfiltration of the plant, notably of the tobacco plant, under vacuum, by agrobacteria comprising a DNA fragment coding for the recombinant protein.

Notably, after five weeks of culture, preferably hydroponically on free mobile floats, agroinfiltration of the tobacco plants is carried out under vacuum, by agrobacteria comprising a DNA fragment coding for the recombinant protein.

This step b) of agroinfiltration may be carried out by any means allowing creation of a vacuum. Preferably, in the method used according to the invention, it is carried out under vacuum by the Venturi effect.

The DNA fragment coding for the recombinant protein, used in step a) and inserted in the agrobacteria, may be prepared by cloning. This DNA fragment may comprise the sequence coding for the recombinant protein, for example a heterologous allergen, said sequence being fused with a sequence encoding a peptide facilitating its purification, for example a "histidine tag" sequence, or a sequence encoding a peptide or a polypeptide for intracellular addressing. Such a peptide or polypeptide for intracellular addressing may notably be selected from the peptides whose sequences are presented in FIG. 8, i.e. from the peptides SEQ ID NO: 1 to 20. The DNA fragment may then be integrated in the pAG01 expression vector developed in the context of the invention (FIG. 1 and sequence SEQ ID NO: 21), and then the agrobacteria are transformed using this expression vector. Preferably, the invention also relates to an expression vector comprising the sequence SEQ ID NO: 21 and an insert, notably located between the right and left bounds of the transfer DNA (TDNA) (this is illustrated in FIG. 1, where the left bound is "LB", and the right bound is "RB"), said insert comprising at least one nucleic acid sequence coding for a peptide selected from SEQ ID NO: 1 to 20, said nucleic acid sequence being directly fused with a second nucleic acid sequence encoding the protein of interest. This vector corresponds to the pAG01 vector comprising an insert, said insert comprising a nucleic acid peptide sequence (selected from SEQ ID NO: 1 to 20) directly fused with the nucleic acid sequence of the allergen of interest. Preferably, the protein of interest is an allergen as described above.

Figure 2:
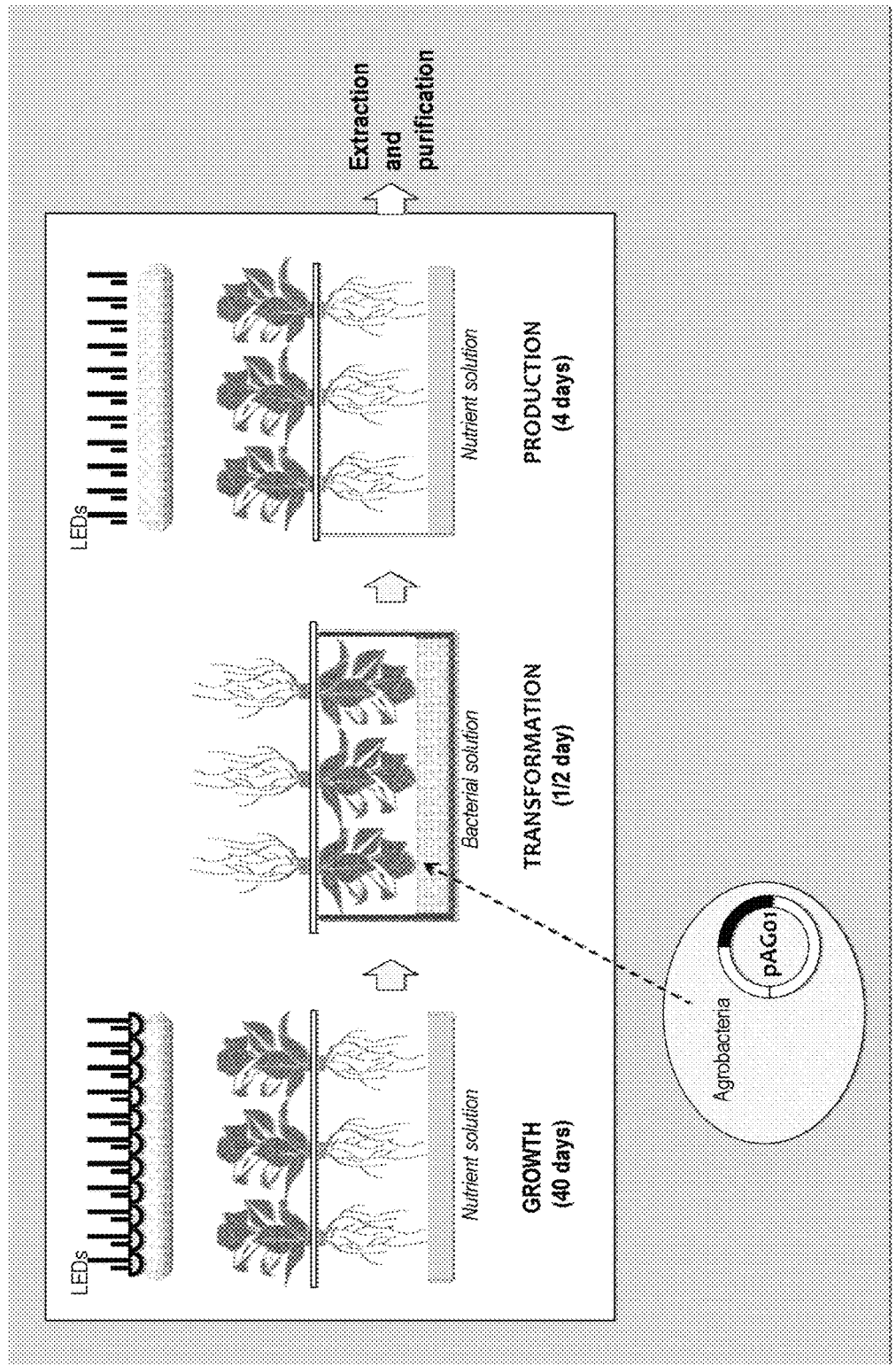
Figure 3:
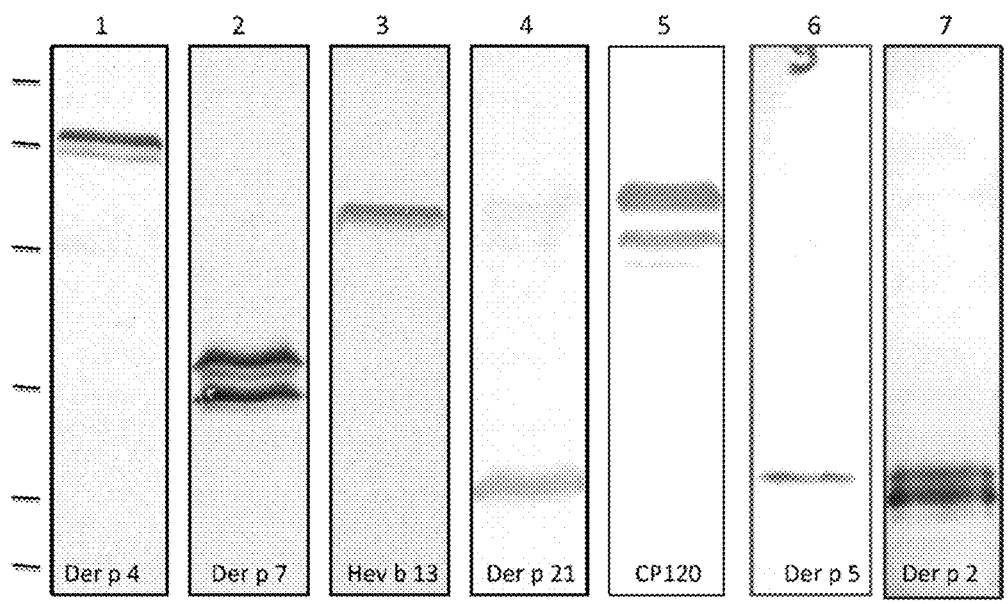

Agroinfiltration of the aerial parts of plants, notably of tobacco plants, notably of *N. benthamiana*, is carried out under vacuum. Preferably, an air-tight chamber is used, which has a system for vacuuming by the Venturi effect. Typically, the chamber contains the culture of agrobacteria and after inverting the floating platforms on which the plants are cultured hydroponically, the latter are immersed, upside down, in the bacterial suspension. This method is illustrated in FIG. 2. It allows simultaneous infiltration of all the plants cultured on one and the same floating platform.

According to a first embodiment, agroinfiltration is carried out by a step of putting the plants under vacuum for 2 minutes.

Preferably, according to a second embodiment, agroinfiltration is carried out in three steps (sequential process):
1) putting under vacuum, preferably at −0.8 bar for 2 minutes,
2) breaking the vacuum, and return to atmospheric pressure preferably for 30 seconds, then
3) putting under vacuum, preferably at −0.8 bar for 2 minutes, followed by return to atmospheric pressure.

This agroinfiltration technique is quick (total duration less than 5 minutes), effective, and easy to automate.

Among the agrobacteria usable according to the invention, we may mention preferably the strains LBA4404, GV3101, EHA 101/105 or C58.

Preferably, the agrobacteria are used for infiltration at a concentration defined by an OD600 between 0.7 and 1.0, in a solution comprising 10 mM of Mes (2-morpholino-ethanesulfonic acid), which may optionally be substituted with MOPS (3-(N-morpholinopropanesulfonic acid), 10 mM of $MgCl_2$ and 100 μM of acetosyringone.

At the end of step b) of agroinfiltration, the method comprises a step c) of returning the plants to culturing, in the same conditions as for step a).

The plants are typically drained upside down for 15 minutes, then put back in culture in the conditions described for step a), ideally ensuring frequent misting of the latter for the first 6 hours of culture following agroinfiltation. Alternatively, the plants are put directly back in culture in the conditions described for step a).

Finally, the method according to the invention comprises a step d) of extraction and purification of the recombinant protein produced after agroinfiltration in step c).

The plant biomass is harvested 4 to 5 days after putting the plants in culture following agroinfiltration.

After grinding and extraction of the proteins from the aerial parts of the plants, the recombinant protein is purified.

The techniques of extraction and purification known from the prior art may be employed in this step. Preferably, if the recombinant protein comprises a "histidine tag" sequence, it is purified by immobilized nickel column chromatography (IMAC), followed by a step of molecular sieving. The tag sequence used for purification may then be cleaved from the end product.

The invention will now be illustrated with the following examples, which are not limiting.

The legends of the figures are as follows:

FIG. 8: Reozyme™ sequences used for targeted expression of recombinant allergens and subcellular storage compartment of the allergens when they are produced in fusion with these addressing peptides. ER: endoplasmic reticulum; GA: Golgi apparatus.

FIG. 1: The T-DNA of the pAG01 vector consists of the two flanking sequences of the T-DNA of the agrobacteria (RB and LB), and of three expression cassettes allowing silencing inhibitor expression (cassette 1), of a recombinant protein preferably an allergen (cassette 2) and of an enzyme conferring resistance to a selection antibiotic or of a protein maturation enzyme (cassette 3).

FIG. 2: The platform developed according to the invention combines original steps and tools that allow low-cost mass production of recombinant allergens of unequalled high quality. Adaptability and speed of production, since 4 to 5 days is sufficient to go from the gene to the protein, are also features of this production platform.

FIG. 3: Production of complex major allergens of the mite *Dermatophagoides pteronyssinus*: Der p 4 (track 1); Der p 7 (track 2); Der p 21 (track 4); Der p 5 (track 6) and Der p 2 (track 7); one of the major allergens of latex: Hey b 13 (track 3) and a mold allergen: CP120 (track 5).

FIG. 4: Schematic illustration of the expression cassettes used (panel A). The expression cassettes include a histidine tag (SEQ ID NO: 22). In panel B, Western blot analyses illustrate the differences in quality of the allergen Der p 2 produced by fusion with different Reozyme™ signals. The allergen is produced in a heterogeneous form and has a noncompliant molecular weight when the Reozyme™ signals R1, R2 and R3 are used. However, when the signal R4 is used, the recombinant allergen is homogeneous and has a molecular weight identical to that of the natural allergen.

FIG. 5: Panel A presents the SDS-PAGE analysis of the total proteins extracted from each plant. Analysis of these extracts by Western blot (panels B and C) illustrates the production yields for one and the same protein of interest, when the plants are cultured either in standard conditions (pot culture+lighting by incandescent lamp) (tracks 1-6, the different tracks correspond to different transformation events), or cultured aeroponically+LED lighting (tracks 7-9). Panel B: chromogenic detection; panel C: detection by chemiluminescence.

FIG. 6: Comparison of expression of the GFP: 1) when agroinfiltration is carried out according to the protocol described in the invention (panel B), or 2) when infiltration is carried out according to a conventional method of infiltration (panel A).

FIG. 7: Analysis by SDS-PAGE and Western Blot of the steps of purification of the allergen Der p 4.

Track 1: Total protein extract.

Track 2: Der p 4 purified on the immobilized nickel column (IMAC) and eluted in the presence of 50 mM of imidazole Track 3: Der p 4 purified by molecular sieving after the IMAC step.

Track 4: Der p 4 purified, whose tag was cleaved in vitro.

Top panel: Analysis of Der p 4 by SDS-PAGE followed by staining of the proteins with Coomassie Blue in the gel.

Bottom panel: Analysis of Der p 4 by SDS-PAGE followed by Western blotting and immunodetection on the print with a specific immunoserum of the purification tag.

EXAMPLE 1: STANDARDIZED PRODUCTION OF COMPLEX ANTIGENS

For validation of the method described here, cDNAs coding for complex allergens of mites, tree or molds were cloned into the pAG01 vector. These vectors were then inserted in the agrobacteria (strain LBA4404) with a view to transient expression in *N. benthamiana.*

The *N. benthamiana* plants were cultured by the method described below: the seeds are sown in earth and cultured for at most 45 days on this substrate. Preferably, the seedlings from these seeds develop for 15 days in this substrate (under LED lighting), before being transferred to tanks for hydroponic culture on free floats. The plants are then cultured for 25 days in these conditions in the presence of nutrients and trace elements, under LED lighting. In an alternative to this protocol, the use of coated seeds allows direct sowing of the *N. benthamiana* plants on the floating platforms. In these conditions, germination and culture of the plants take place in hydroponic conditions.

After culture for 40 days, the plants maintained on the floats are transferred to an air-tight chamber for transfection. For penetration of the agrobacteria bearing the binary vector, the aerial part of the plants is immersed (float inverted) in the solution of agrobacteria whose concentration corresponds to OD 600: 0.7. Transfection is carried out under vacuum in the air-tight chamber by the Venturi effect according to the following protocol: 2 min under vacuum (−0.8 bar), return to normal, then again 2 min under vacuum (−0.8 bar). The floats are then put on supports (plants upside down) for 10 to 15 min, so that the plants drain. Then the plants, still held on the floating platforms on which they were cultured, are put back in the culture tanks for 4 days, ideally ensuring frequent misting of the latter for the first 6 hours of culture following agroinfiltation.

After these 4 days, the aerial parts of the plants expressing the various allergens are harvested. The proteins are extracted in a denaturing buffer and then analyzed by SDS-PAGE and/or Western blotting using an antibody directed against the FLAG epitope.

FIG. 3 illustrates the results obtained. The method according to the invention allows production of complex major allergens.

EXAMPLE 2: THE METHOD ACCORDING TO THE INVENTION ALLOWS QUALITY CONTROL OF THE ALLERGENS

In order to monitor the maturation and the homogeneity of the recombinant allergens, different signals (R1, R2, R3 and R4) were fused with the allergen of interest, and then the fusion protein was cloned into the pAG01 vector. These vectors were then inserted in the agrobacteria (strain LBA4404) with a view to transient expression in *N. benthamiana.*

The *N. benthamiana* plants were cultured by the method described below: the seeds are sown in earth and the seedlings from these seeds develop for 15 days in this substrate (LED lighting) before being transferred to free floats. The plants are then cultured for 25 days hydroponically on free floats.

After culture for 40 days in these conditions, the plants maintained on the floating culture platforms are transferred to an air-tight chamber for transfection. For penetration of the agrobacteria bearing the binary vector, the aerial parts of the plants are immersed (float inverted) in the solution of agrobacteria. Transfection is carried out under vacuum in the air-tight chamber by the Venturi effect according to the following protocol: 2 min under vacuum (−0.8 bar), return to normal, then again 2 min under vacuum (−0.8 bar). The floats are then put on supports (plants upside down) for 10 to 15 min so that the plants drain. Then the plants, still held on the floats, are put back in the culture tanks for 4 days.

After these 4 days, the plants expressing the various allergens are harvested. The proteins are extracted by grinding the aerial parts in a denaturing buffer and then analyzed by SDS-PAGE and/or Western blotting using an antibody directed against the FLAG epitope.

Figure 4:
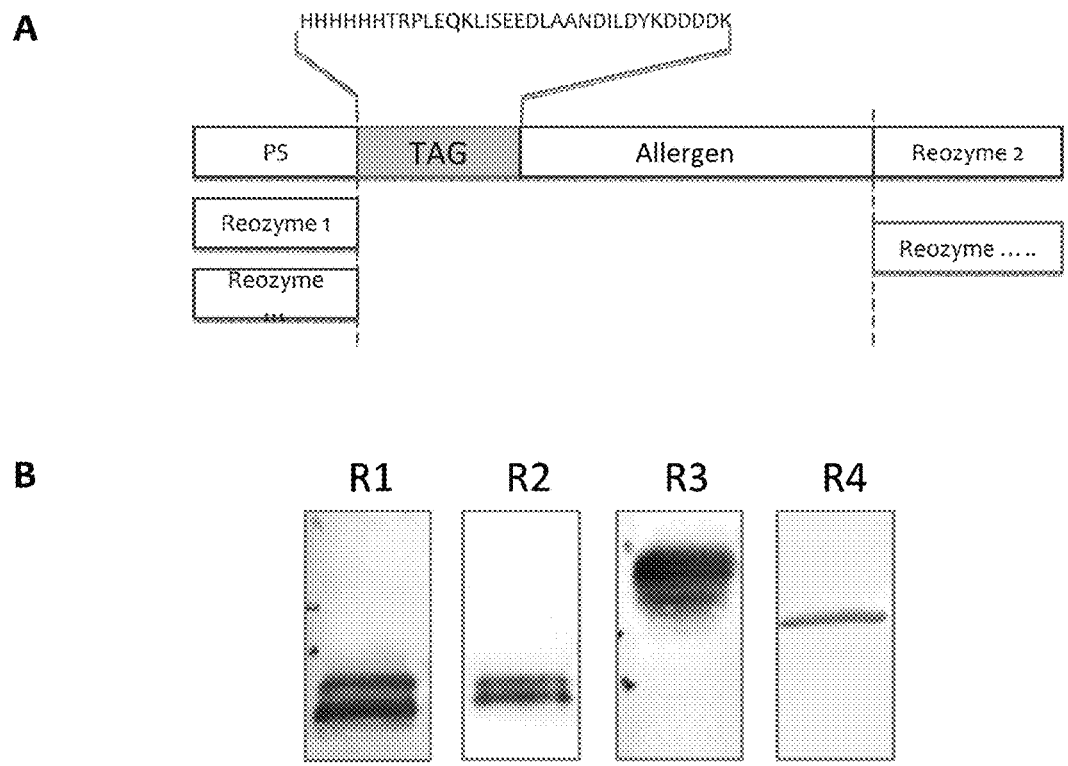

FIG. 4 presents a schematic illustration of the expression cassettes used (panel A). The expression cassettes include a histidine tag (SEQ ID NO: 22). It also shows, with the example of the mite allergen Der p 2, the qualitative advantages associated with using the Reozyme™ signals. In fact, in panel B, Western blot=analyses illustrate the differences in quality of the allergen Der p 2 produced by fusing with different Reozyme™ signals. The allergen is produced in a heterogeneous form and has a noncompliant molecular weight when the Reozyme™ signals R1, R2 and R3 are used. However, when signal R4 is used, the recombinant allergen is homogeneous and has a molecular weight identical to that of the natural allergen.

EXAMPLE 3: THE METHOD ACCORDING TO THE INVENTION ALLOWS A HITHER YIELD

For this example, we compared the use of the pAG01 vector coupled with the use of the method described in the invention with the use of a binary vector (−/+ silencing inhibitor) coupled to conventional methods of transfection described for example in Medrano et al. (2009).

The cDNA encoding the allergen Der p 7 of *Dermatophagoides pteronyssinus* was cloned either into the pAG01 vector, or into the pBI121 vector. These vectors were then inserted in the agrobacteria (strain LBA4404) with a view to transient expression in *N. benthamiana*.

Then the strains of agrobacteria were used for transfecting plants cultured either hydroponically on floating platforms as described in examples 1 and 2, or cultured in earth and then infiltrated under vacuum according to a conventional protocol as published in Pogue et al. (2010).

Figure 5:
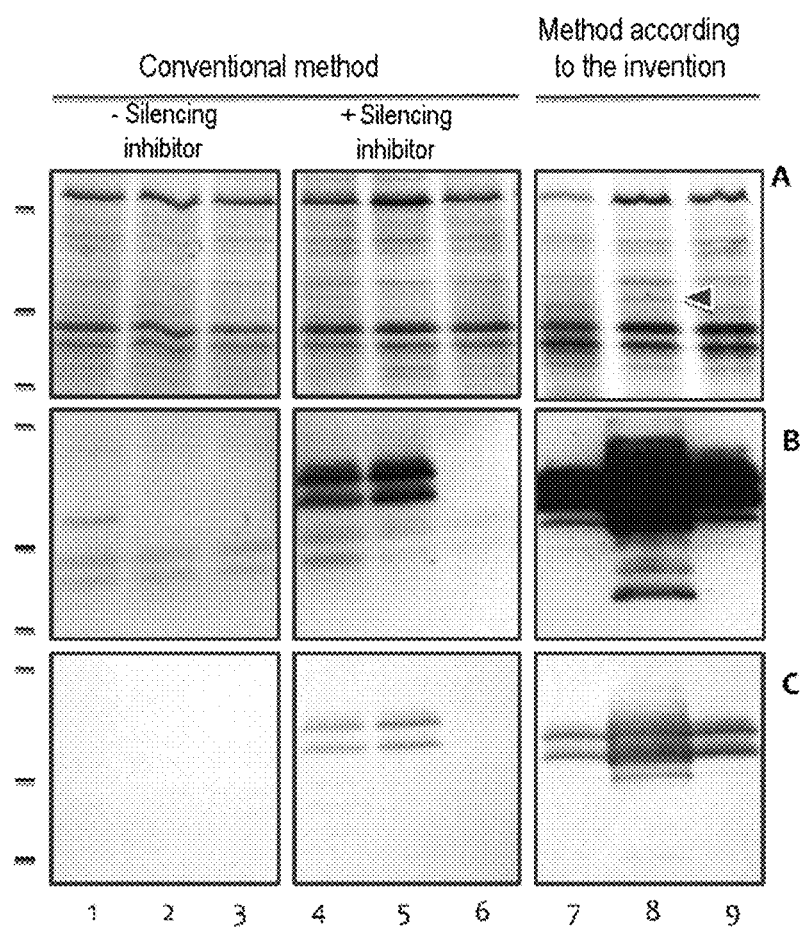

As illustrated in FIG. 5, the plant culture conditions described in the method, as well as the use of the pAG01 vector, allow higher yields of recombinant allergens than those observed with the conditions generally used for transient expression.

It can clearly be seen from FIG. 5 that the yields of the method according to the invention are far higher than those obtained with a conventional method. Moreover, the inventors demonstrate better homogeneity of the various transformation events, as illustrated by tracks 7 to 9 compared to tracks 4 to 6.

Figure 6:
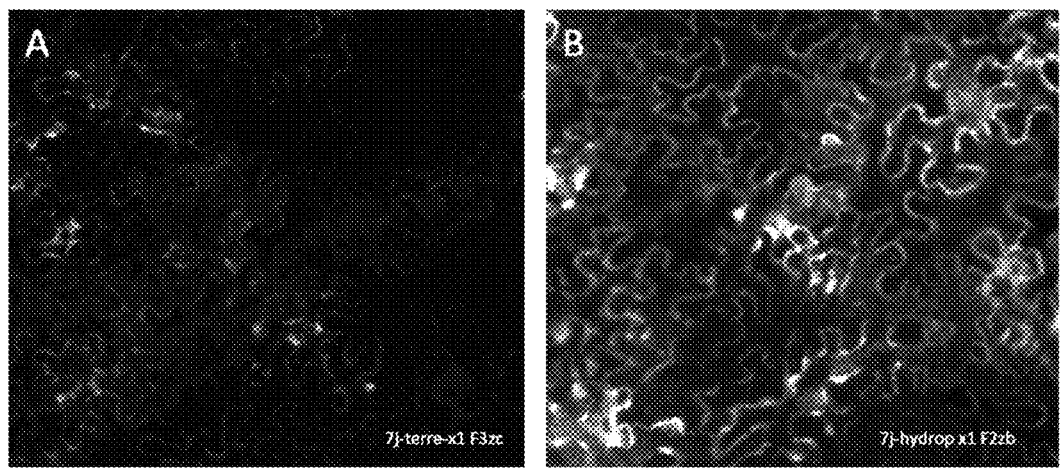

The higher expression levels observed for Der p 7 are partly explained by the conditions of agroinfiltration according to the method of the invention. In fact, as illustrated in FIG. 6, infiltration of the foliar tissues is more effective, as is described in the method. In this figure, the inventors compared the expression of GFP: 1) when agroinfiltration is carried out according to the protocol described in the invention (panel B), or 2) when infiltration is carried out according to a conventional method of infiltration (panel A) described for example in Medrano et al. (2009).

EXAMPLE 4: THE METHOD ACCORDING TO THE INVENTION ALLOWS EASY PURIFICATION

The leaves of the *Nicotiana benthamiana* plants are collected, and the proteins are extracted by grinding this plant material in a phosphate buffer supplemented with NaCl (0.1 M), pH 7.5. After quick filtration, the extract is deposited on an immobilized nickel column. The proteins of the extract that do not have affinity for the chromatography matrix are not retained on the column. However, the recombinant allergens produced according to the method have a hexa-histidine tag and are retained on this type of matrix. After washing the column to remove the contaminating proteins, the allergens are eluted specifically in the presence of 50 mM imidazole in phosphate buffer.

The method of production according to the invention is flexible and easily adaptable to the production of any allergen of interest. This is true not only of the techniques for culture, cloning, agroinfiltration, and extraction, but also for purification.

Figure 7:
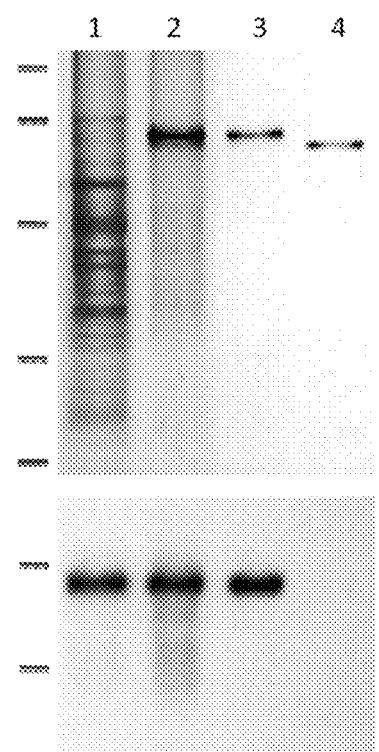

In fact, owing to fusion of a tag, purification of the recombinant allergens is standardized. This is illustrated in FIG. 7, which presents analysis by SDS-PAGE and Western blotting of the steps of purification of the allergen Der p 4 produced as described in the invention. This analysis illustrates the method of purification of this allergen in two chromatography steps:

1) immobilized nickel affinity column (IMAC) and 2) molecular sieving.

Track 1: Total protein extract.

Track 2: Der p 4 purified on the immobilized nickel column (IMAC) and eluted in the presence of 50 mM of imidazole Track 3: Der p 4 purified by molecular sieving after the IMAC step.

Track 4: Der p 4 purified, whose tag was cleaved in vitro.

Top panel: Analysis of Der p 4 by SDS-PAGE followed by staining of the proteins with Coomassie Blue in the gel.

Bottom panel: Analysis of Der p 4 by SDS-PAGE followed by Western blotting and immunodetection on the print with a specific immunoserum of the purification tag.

The invention claimed is:

1. A method for producing a recombinant allergen in a plant, the method comprising the following steps:
   a) culturing the plant aeroponically or hydroponically, then
   b) agroinfiltrating the plant obtained in a), under vacuum, with agrobacteria comprising an expression vector obtained by modifying the vector pAG01 (SEQ ID NO: 21) by inserting a DNA fragment into cassette 2 in FIG. 1, wherein the DNA fragment encodes the recombinant allergen, then
   c) returning the plants to culture, in the same conditions as for the culture in step a), then
   d) extracting and purifying the recombinant allergen from aerial parts of the plants produced in step c).

2. The method of claim 1, wherein the recombinant allergen is selected from the group consisting of: allergens of *Dermatophagoides farinae*, allergens of *Dermatophagoides pteronyssinus*, allergens of *Euroglyphus manei*, allergens of *Acarus siro*, allergens of *Blomia tropicalis*, cockroach allergens, tree allergens, grass allergens, & pollen allergens, allergens of animals, allergens of molds, allergens of hevea latex and allergens responsible for food allergies.

3. The method of claim 1, wherein the recombinant allergen is selected from the group consisting of Der f 10, Der f 11, Der f 13, Der f 14, Der f 15, Der f 16, Der f 17, Der f 18, Der f 2, Der f 2.0101, Der f 2.0102, Der f 2.0103, Der f 2.0104, Der f 2.0105, Der f 2.0106, Der f 2.0107, Der f 2.0108, Der f 2.0109, Der f 2.0110, Der f 2.0111, Der f 2.0112, Der f 2.0113, Der f 2.0114, Der f 2.0115, Der f 2.0116, Der f 2.0117, Der f 20, Der f 3, Der f 4, Der f 5, Der f 6, Der f 7, Der f 8, Der f 9 and Der f HSP70.

4. The method of claim 1, wherein the recombinant allergen is an allergen of *Dermatophagoides pteronyssinus* selected from the group consisting of Der p 10, Der p 11, Der p 14, Der p 15, Der p 18, Der p 2, Der p 2.0101, Der p 2.0102, Der p 2.0103, Der p 2.0104, Der p 2.0105, Der p 2.0106, Der p 2.0107, Der p 2.0108, Der p 2.0109, Der p 2.0110, Der p 2.0111, Der p 2.0112, Der p 2.0113, Der p 20, Der p 21, Der p 3, Der p 4, Der p 5, Der p 6, Der p 7, Der p 8 and Der p 9.

5. The method of claim 1, wherein the recombinant allergen is selected from the group consisting of Blo t 1, Blo t 5, Blo t 9, Blo t 10, Blo t 12 and Blo t 21.

6. The method of claim 1, wherein the agroinfiltrating is carried out under vacuum by Venturi effect.

7. The method of claim 6, wherein the agroinfiltrating is carried out either by a step of putting the plant under vacuum for 2 minutes, or
   by putting the plant under vacuum, then breaking the vacuum and returning to atmospheric pressure, then putting under vacuum, followed finally by return to atmospheric pressure.

8. An expression vector, obtained by modifying the vector pAG01 (SEQ ID NO: 21) by inserting a DNA fragment into cassette 2 in FIG. 1, wherein the DNA fragment comprises at least one nucleic acid sequence coding for a peptide selected from SEQ ID NO: 1 to 20, the nucleic acid sequence being directly fused with a second nucleic acid sequence encoding a protein of interest.

9. The expression vector of claim 8, wherein the protein of interest is an allergen.

10. The expression vector of claim 8, wherein the protein of interest is selected from the group consisting of allergens of *Dermatophagoides farinae*, allergens of *Dermatophagoides pteronyssinus*, allergens of *Blomia tropicalis*, allergens of *Euroglyphus manei*, allergens of *Acarus siro*, cockroach allergens, tree allergens, grass allergens, pollen allergens, allergens of animals, allergens of molds, allergens of hevea latex and allergens responsible for food allergies.

11. The method of claim 1, wherein the plant is *Nicotania benthamiana*.

12. The method of claim 1, wherein the plant is cultured under LED lighting.

13. The method of claim 6, wherein the agroinfiltrating is carried out by putting the plant under vacuum at −0.8 bar for 2 minutes, then breaking the vacuum and returning to atmospheric pressure for 30 seconds, then putting under vacuum at −0.8 bar for 2 minutes, followed finally by return to atmospheric pressure.

14. The method of claim 1, wherein the recombinant allergen is a dust mite allergen.

15. The method of claim 1, wherein the recombinant allergen is an allergen of animals.

16. The method of claim 1, wherein the recombinant allergen is an allergen responsible for food allergies.

17. The expression vector pAG01 consisting of the sequence SEQ ID NO: 21.

* * * * *